United States Patent [19]

D'Alfonso et al.

[11] Patent Number: 5,896,166
[45] Date of Patent: Apr. 20, 1999

[54] REMOTE CCD VIDEO CAMERA WITH NON-VOLATILE DIGITAL MEMORY

[75] Inventors: David A. D'Alfonso, Goleta; Jordan C. Christoff, Santa Barbara, both of Calif.

[73] Assignee: Envision Medical Corporation, Goleta, Calif.

[21] Appl. No.: 08/589,875

[22] Filed: Jan. 23, 1996

Related U.S. Application Data

[63] Continuation of application No. 08/459,285, Jun. 2, 1995.
[51] Int. Cl.⁶ .............................. H04N 7/18; A61B 1/00
[52] U.S. Cl. ....................... 348/72; 348/75; 348/76
[58] Field of Search .......................... 348/76, 74, 72, 348/65, 82, 83, 84, 85

[56] References Cited

U.S. PATENT DOCUMENTS

| | | | |
|---|---|---|---|
| 3,885,091 | 5/1975 | Fish et al. | 348/84 |
| 4,302,772 | 11/1981 | Gillot | 348/82 |
| 4,391,282 | 7/1983 | Ando et al. | 128/4 |
| 4,539,586 | 9/1985 | Danna et al. | 348/75 |
| 4,539,588 | 9/1985 | Ariessohn et al. | 348/83 |
| 4,621,643 | 11/1986 | New, Jr. et al. | 128/633 |
| 4,657,013 | 4/1987 | Hoerenz et al. | 606/4 |
| 4,667,230 | 5/1987 | Arakawa et al. | |
| 4,700,708 | 10/1987 | New, Jr. et al. | 128/633 |
| 4,746,975 | 5/1988 | Ogiu | 348/76 |
| 4,770,179 | 9/1988 | New, Jr. et al. | 128/633 |
| 4,822,997 | 4/1989 | Fuller et al. | 364/550 |
| 4,862,393 | 8/1989 | Reid et al. | 364/550 |
| 4,868,646 | 9/1989 | Tsuji | 348/76 |
| 4,893,185 | 1/1990 | Fukushima et al. | |
| 4,897,789 | 1/1990 | King et al. | 604/6 |
| 4,926,258 | 5/1990 | Sasaki et al. | 348/72 |
| 4,975,864 | 12/1990 | Sendall et al. | |
| 4,977,394 | 12/1990 | Manson et al. | 340/679 |
| 4,982,351 | 1/1991 | Kawate et al. | |
| 4,996,975 | 3/1991 | Nakamura | 128/6 |
| 5,016,198 | 5/1991 | Schreiber | |
| 5,021,888 | 6/1991 | Kondou et al. | |
| 5,036,396 | 7/1991 | Miyabayashi | |
| 5,040,068 | 8/1991 | Parulski et al. | |
| 5,071,401 | 12/1991 | Salvati et al. | |
| 5,089,979 | 2/1992 | McEachern et al. | |
| 5,095,368 | 3/1992 | Miyakawa et al. | |
| 5,101,271 | 3/1992 | Andrews | |
| 5,155,693 | 10/1992 | Altmayer et al. | 364/550 |
| 5,162,725 | 11/1992 | Hodson et al. | 324/115 |
| 5,359,993 | 11/1994 | Slater | 600/133 |
| 5,400,267 | 3/1995 | Denen et al. | 364/552 |

*Primary Examiner*—Bryan Tung
*Attorney, Agent, or Firm*—Lyon & Lyon LLP

[57] ABSTRACT

A video camera system stores operating parameter information for reading by the system to provide optimum operating conditions, collects information reflecting system uses for later reading by the system to provide a performance history, and is relatively small and operates with a reduced number of electrical lines to transmit electrical information.

15 Claims, 3 Drawing Sheets

REMOTE CCD VIDEO CAMERA WITH NON-VOLATILE DIGITAL MEMORY

This application is a continuation of application Ser. No. 08/459,285, filed Jun. 2, 1995.

I. BACKGROUND OF THE INVENTION

The field of the invention relates generally to video cameras, and more specifically to video camera systems which may store operating parameter information, and which may collect information reflecting uses of the system. The camera system may then use the information to operate at optimum conditions, to provide a performance history or for other reasons.

In the recent past, the need for small, lightweight video cameras using a solid state image sensor such as a charge coupled device ("CCD"), charge injection device ("CID") or metal oxide semiconductor ("MOS") has rapidly developed for both medical and industrial applications. One medical application involves a CCD which is attached to an endoscope to observe a surgical site. In this arrangement, the CCD may be contained in a small camera head and attached to the endoscope eyepiece so that the camera head/endoscope combination, or video-endoscope, is lightweight and easily manipulable by a surgeon. A flexible cable connects the camera head to the rest of the camera electronics which are usually included in a camera control unit located at a remote location. The camera control unit includes control and video processing circuitry which send operating signals to the CCD and receive signals from the CCD which are processed for video display. The camera control unit is also coupled to a video monitor for viewing of the surgical site by one or more physicians.

An industrial application employing a CCD involves observation of industrial processes where direct observation by a person is unsafe or otherwise impractical. Such processes include those occurring in nuclear power generating stations, furnaces or engine compartments, or other processes which are generally inaccessible. Here, a camera head including a CCD may be attached to a hole in the wall of the vessel in which the process occurs. The camera head is then connected by cable to a camera control unit and video monitor at a remote location in similar fashion described above.

The type of CCD or other solid state image sensor used for various medical or industrial applications may differ. However, all solid state imagers are not exactly alike, and to achieve peak or even acceptable performance, each solid state imager must be operated by the camera control unit at the imager's particular operating parameters. For example, different CCDs operate at varying substrate voltages and if the control unit supplies too much voltage to the CCD, the resulting video display exhibits noise and interference. Essentially, each CCD or other imager has its own personality that should be known to the camera control unit for the CCD to produce an optimum video picture signal. While it may be possible to provide different control units to accommodate the varying operating parameters of various imagers, such an arrangement is expensive and generally impractical. Thus an existing problem is poor interchangeability of imagers with camera control units or the sacrifice of optimum imager operating conditions and video display. This problem is significant because for example, different CCDs are typically used in connection with the same camera control unit.

For example, during a surgical procedure a problem may arise with the camera head requiring its, and the CCD's, replacement. Also, video-endoscopes where the camera head is permanently attached to the endoscope are now used but a surgical procedure may require more than one type of endoscope and thus more than one CCD. To avoid changing the control unit, and to avoid sacrificing video quality, time-consuming adjustments to the control unit to vary the signals it sends to operate the CCD are necessary. However, because the control unit is typically located outside the arbitrary sterile area surrounding the patient, an additional technician is necessary to effect adjustments, or a physician effects adjustments who then must again undergo sterilization or risk contamination. Accordingly, there is a need for interchangeability of CCDs or other imagers (and the camera heads or other devices which contain them) with camera control units without sacrificing video display, and without the need for time-consuming control unit adjustments.

In addition to the lack of interchangeability, existing camera systems are generally incapable of collecting information to record uses of the camera system to provide a performance history. Such information may be useful for example, to determine when the camera system needs maintenance. Accordingly, there is also a need for a video camera system which may collect operating history information during the camera system's life so that this information may be later used by the system or operator. There is also a need for a camera system which provides these benefits but is relatively small and manipulable.

II. SUMMARY OF THE INVENTION

In a first aspect of the invention, a video camera system is described which may store operating parameter information, which information may be read by the system to provide optimum operating conditions when the video camera is used.

In another aspect of the invention, a video camera system is described which may collect and store information reflecting system uses, which history information may be read by the system for adjustment, maintenance or other purposes.

In another aspect of the invention, a video camera system is described which provides the above and other advantages but which is relatively small and which operates with a reduced number of electrical lines to transmit electrical information.

Additional advantages and objects of the invention appear in the description below, or will be apparent to those of ordinary skill in the art who practice the invention.

III. BRIEF DESCRIPTION OF THE FIGURES

IV. DESCRIPTION OF THE PREFERRED EMBODIMENT

Figure 1:
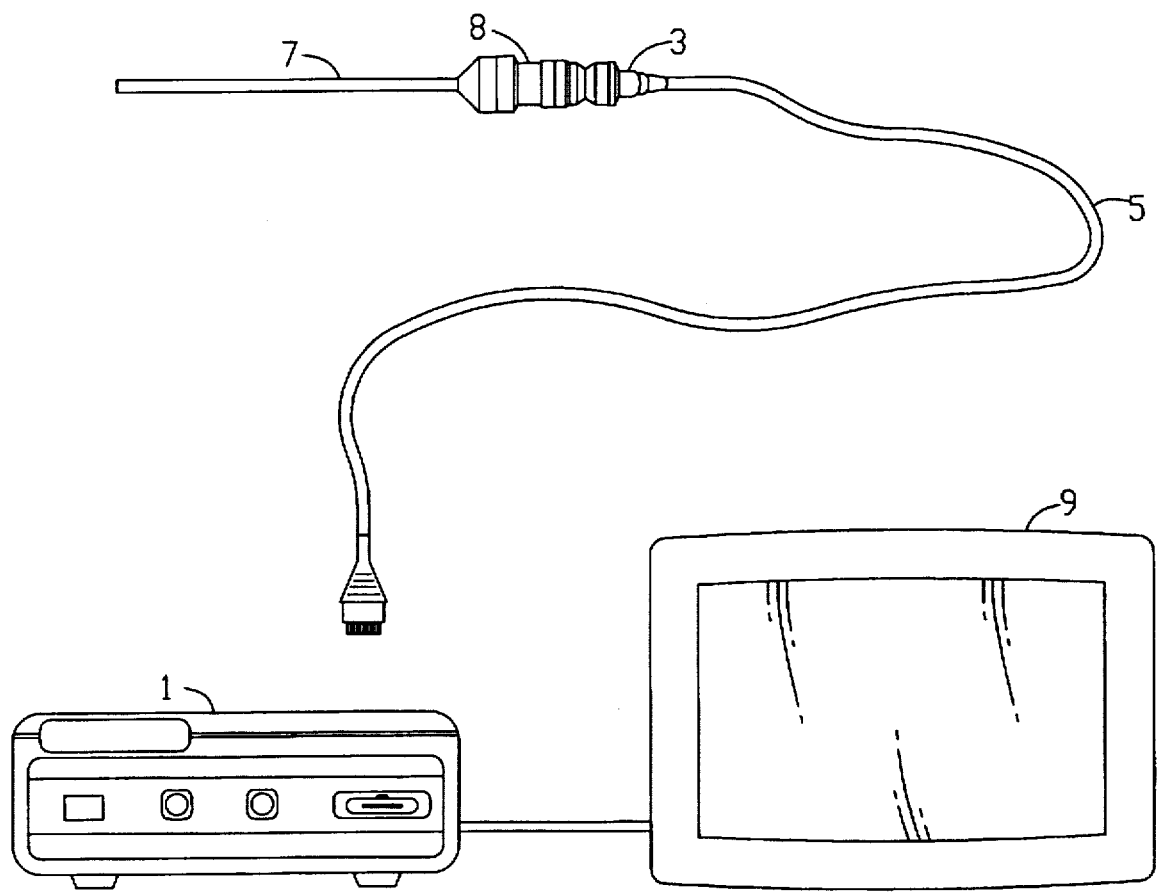
FIG. 1 is a video camera system for use in endoscopy.

Referring to FIG. 1, a video camera system for use in endoscopy is shown. Camera control unit 1 is coupled to camera head 3 by cable 5. Camera head 3 is coupled to endoscope 7 by an optical coupler 8. The video signals produced ultimately appear as a video display on monitor 9. Cable 5 may be permanently attached to camera head unit 3 to maintain a tight seal thereby protecting the components contained therein from contaminants. Alternatively, cable 5 may be removably attached to camera head 3. The camera head 3 may be permanently attached to endoscope 7 or removably attached thereto.

Figure 2:
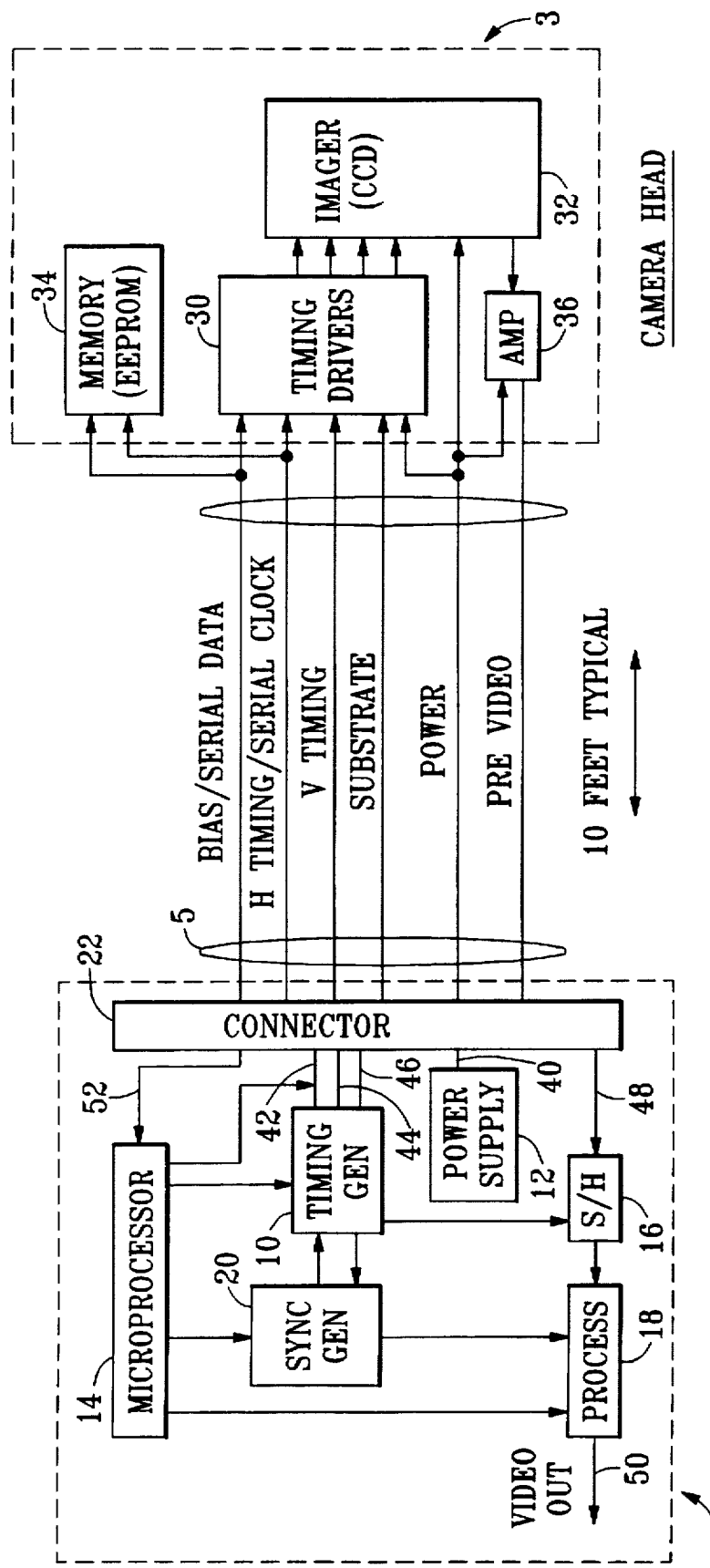
FIG. 2 is a block diagram showing a camera control unit and camera head connected together by a cable.

Referring to FIG. 2, the camera control unit 1 may include timing signal generator 10, power supply 12, processing means such as a microprocessor 14, sample and hold circuitry 16, process circuitry 18, and sync generator 20. As an alternative, microprocessor 14 may be supplemented or replaced with other suitable processing means such as programmable logic which performs the functions described in connection with microprocessor 14 herein. Camera control unit 1 may also include connector 22 which couples the camera control unit 1 to the cable 5. The camera head unit 3 may include timing driver circuitry 30, solid state image sensor 32, such as a CCD, non-volatile memory device 34 and amplifier 36. Camera head 3 is preferably small for easy manipulation by a physician in a medical procedure, or for observing industrial processes providing limited space for the camera head. If a permanent or semi-permanent coupling exists between the camera head 3 and cable 5, the camera head 3 effectively includes the cable 5.

Power supply 12 provides power to the timing driver circuitry 30, solid state imager 32 and amplifier 36 via signal line 40 in cable 5. Timing generator 10 generates H and V timing signals on lines 42 and 44 respectively, as well as a substrate voltage on line 46, which are all sent to the timing driver circuitry 30. Microprocessor 14 or some other processing means provides a bias signal over line 52 to timing circuitry 30. Timing circuitry 30 then provides the bias signal, H and V driving signals and substrate voltage to the imager 32. Imager 32 generates an image, or pre-video signal, which passes through amplifier 36 and returns to the camera control unit 1 through the pre-video line 48. The pre-video signal is then received in turn by the sample and hold circuitry 16 and the processing circuitry 18 which serve to generate a video out signal along line 50 which is sent to other electronics and the video monitor 9.

Microprocessor 14 and sync generator 20 may be coupled to the components of control unit 1 by the various lines shown in FIG. 1. Microprocessor 14 is also coupled to memory device 34 by serial clock line 42 and serial data line 52. Those skilled in the art will recognize that different components and arrangements thereof may be used in addition to and/or in lieu of those shown in the control unit 1 and camera head 3 of FIG. 1.

Figure 3:
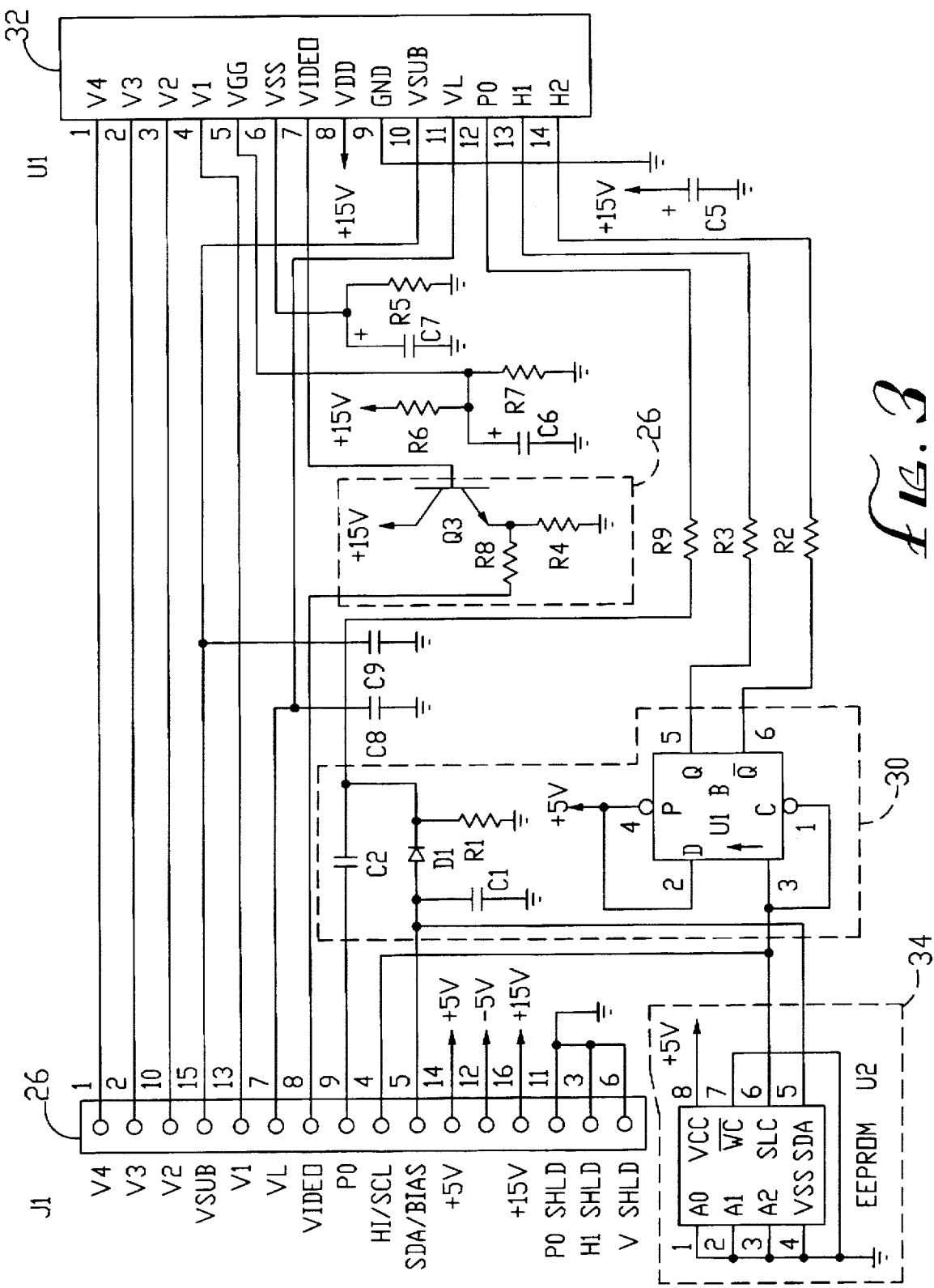
FIG. 3 is a schematic of a camera head.

Referring to FIG. 3, a schematic showing preferred circuitry of camera head 3 is shown. The connector 26 shown in FIG. 3 may be incorporated into the camera head 3 at the location where cable 5 is coupled thereto. Alternatively camera head 3 may not include a connector (e.g., in an embodiment where the cable 5 and camera head 3 are permanently joined), such that connector 26 is contained in control unit 1 as is connector 22 in FIG. 2. The dashed boxes generally represent the memory device 34, timing driver circuitry 30 and amplifier 26.

As shown, the V timing signals V1, V2, V3 and V4 are respectively provided by connector pins 13, 10, 2 and 1 and may pass directly to the imager 32. Alternatively as shown in FIG. 2, the V timing signals may be processed by the timing driver circuitry 30 before passing to imager 32. The substrate voltage, VSUB, is provided by pin 15 and passes directly to the imager 32, or alternatively may first be processed by the timing driver circuitry 30. Power supply signal VL (i.e., typically the lowest voltage supplied by the power supply) is provided by pin 7 and passes to the imager 32. Pin 8 of connector 26 receives the pre-Patent video signal generated by imager 32 after this signal has been processed by amplifier 26 as shown. The PG or pre-charged gate reference signal, against which the actual pixel light values of imager 32 are measured, is provided by pin 9 and is processed by the timing driver circuitry 30 before passing to imager 32.

The H1 timing and serial clock signals are both provided by pin 4. As discussed later, this line-sharing capability is possible because these two signals are preferably transmitted during different phases of the camera system's use. H timing signals which are generally transmitted when the imager 32 operates, are processed by the timing driver circuitry 30 and are then passed to the imager 32. Serial clock signals which are generally transmitted during the turn-on and turn-off phases before and after imager operation, pass directly to the memory device 34. The serial data and bias signals are both provided by pin 5 and also exhibit line-sharing capability in similar fashion.

The +5 v, −5 v and +15 v signals respectively provided by pins 14, 12 and 16 are typical voltages provided by a power supply. In FIG. 3, the −5 v line is not used. However, the +5 v signal is transmitted to the timing driver circuitry 30 and memory device 34 as well as the other locations shown. The +15 v signal is transmitted to the imager 32, amplifier 26 and other locations shown. The PG, H1 and V Shield signals respectively provided by pins 11, 3 and 6 act as shields for the PG, H1 and Video signals. Those skilled in the art will recognize that different component and line configurations may be used.

Referring back to FIG. 2, in a preferred embodiment information reflecting the properties and operating parameters specific to a certain imager such as a CCD 32, camera head 3 and associated components may be stored in a digital non-volatile memory device 34 such as an electrically erasable programmable memory ("EEPROM"). In this preferred embodiment, when camera head 3 is coupled to control unit 1, microprocessor 14 may read the stored information through serial clock and data lines 42, 52. As described in detail below, the microprocessor 14 may then use this information to adjust the circuitry of control unit 1 so that control unit 1 sends the proper operating signals to imager 32.

Also in a preferred embodiment, in addition to storing information to be read by microprocessor 14, the memory device 34 may receive information from the control unit 1 or some other source throughout the video camera system's life. For example, the microprocessor 14 may preferably write to the memory device 34. As discussed later, this allows a compilation of data representing the camera system's operating history which serves various useful purposes.

A suitable EEPROM which is capable of both these reading and writing functions is Exel Microelectronics model no. XL24C04. A suitable microprocessor which may read the memory device 34 and responsively adjust the circuitry of the control unit 1, as well as write to the memory device 34, is Motorola model no. 68HC16.

Storage of information by memory device 34 for reading by microprocessor 14 is now further described. This is followed by further description of how memory device 34 may collect information or have information written to it, followed by description of the attributes contributing to the relatively small size and reduced number of electrical lines of the preferred embodiment.

The memory device 34 may be initially programmed with information describing the operating parameters of the particular imager 32 such as a CCD, and camera head 3 with which the memory device 34 will be associated. A suitable programmer may be used at the manufacturer's facility to load data into the memory device 34 before the camera head 3 is shipped. Alternatively as described later, the control unit 1 may write operating parameter information to the memory device 34.

When the video camera system is to be used, microprocessor 14 may read the operating parameter information stored in memory device 34 and adjust the various circuitry in control unit 1, if necessary, so that the signals sent to the camera head 3 are those which provide optimum operating conditions for the imager 32. Alternatively, another suitable processing means such as programmable logic may be used with or in lieu of microprocessor 14 to provide this capability. By optimum parameters, operation or conditions, it is meant that the control unit 1 generally operates the imager 32 and/or camera head unit 3 under conditions which ultimately provide an acceptable video monitor display. It is not intended that optimum parameters, operation or conditions necessarily provide an absolutely ideal video display.

Preferably, microprocessor 14 reads the stored information each time the camera head 3 is operated so that the optimum operating parameters are established for each use. In the preferred embodiment, microprocessor 14 communicates with memory device 34 during the turn-on and/or turn-off phases of camera head 3 through serial clock and data signals over lines 42 and 52. These signals are preferably not transmitted when the CCD is generating a video signal between turn-on and turn-off so that lines 42 and 52 may respectively transmit the H timing signal and bias signal during imager 32 operation. This line-sharing capability is described later.

The types of information which may be stored and reading thereof are now further described. Operating parameter information stored in memory device 34 may include the proper operating substrate voltage of the imager 32 such as a CCD. Upon reading this information, microprocessor 14 may adjust timing generator 10 so that the proper substrate voltage is delivered to the CCD 32 to avoid interference on the video monitor which would occur if the wrong substrate voltage is supplied. The television format (e.g. NTSC or PAL) of the imager 32 may also be stored in memory device 34. Upon reading this information, microprocessor 14 may adjust the correction algorithms used in connection with the sync generator 20 or timing generator 10 so that the control unit 1 properly operates either NTSC or PAL-formatted camera heads.

For endoscopic applications, memory device 34 may also include information describing the type of endoscope with which the camera head 3 will be fitted. For example, if a flexible endoscope is used, memory device 34 could inform microprocessor 14 to instruct control unit 1 to compensate for the reduced light, and to invoke picture improvement software to eliminate the honeycomb pattern of the bundled individual optic fibers, which characteristics are usually synonymous with flexible endoscopes.

Information representing the imager's color filter array pattern may also be stored. This information is important to optimum operation because the image signal from a CCD, CID or MOS imager is color dependent and color filter patterns vary between imagers such as CCDs, especially those having individual color filters over each pixel, and the pattern also affects initial white balance values. Information representing the number of CCDs or other imagers contained in the camera head 3 which may affect color filter array pattern information, may also be stored. For example, memory device 34 may store information that the camera head 3 contains multiple CCDs as described in pending U.S. application Ser. Nos. 07/934,815, filed Aug. 24, 1992 and entitled Remote 3D Video Camera System, and 08/018,053, filed Feb. 16, 1993 and entitled Sterilizable CCD Video Camera, both assigned to Envision Medical Corp., the disclosure of both of which are expressly incorporated by reference herein.

Other information which does not relate solely to the imager 32 or camera head 3 may also be stored in the memory device 34. For example, cable length information may be stored so that the microprocessor 14 may adjust phase detection and correction circuitry (not shown) in the control unit 1 to compensate for the various signal delays that occur due to cables having different lengths. Such compensation circuitry is described in pending U.S. application Ser. No. 07/951,123, filed Sep. 25, 1992 and entitled Video Camera Compensation Circuitry, and assigned to Envision Medical Corp., the disclosure of which is expressly incorporated by reference herein. Adjustments to compensation circuitry is especially useful if the camera head 3 will be coupled to cables of varying lengths.

As another example, with respect to video-endoscopes as shown in FIG. 1, information describing endoscope 7 characteristics and the aperture size and type of optics used in the optical coupler 8 which may affect how the automatic light level and gain circuits should operate, may also be stored. The memory device 34 may also store information which when read, will confirm whether camera head 3 and control unit 1 are compatible. From an original equipment manufacturer's point of view, it may not be desirable for all camera heads to operate with all control units. For example, it may be undesirable for camera heads that are custom configured for one customer to operate when connected to another customer's control unit.

It will be recognized by those skilled in the art that the memory device 34 may store information other than that explicitly discussed above, and that the microprocessor 14 or other suitable processing means such as programmable logic, may communicate with other components which may be within the control unit 1 and in other manners than those expressly discussed above. Thus in the preferred embodiment, the control unit 1 reads the memory device 34 and adjusts the control circuitry to provide optimum operating conditions for the imager 32.

The writing capabilities of the preferred memory device 34 are now further described. As mentioned above, memory device 34 preferably comprises an EEPROM to which the microprocessor 14 or other processing means such as programmable logic may write data at any time during the life of the camera head 3 for later recall. This is an advance over prior apparatus using "read only" memory devices which may be programmed only once, usually at the time of manufacture and before the memory device is mounted in the apparatus.

Preferably, microprocessor 14 or other processing means writes to the memory device 34 during the turn-on and/or turn-off phases each time the camera head 3 is used and not during imager operation to provide the line-sharing benefit mentioned above and discussed later. By writing to the memory device 34 each time the camera head 3 is used, characteristics describing each use such as the length of operation time, the white balance levels at which the imager 32 initially operated and other characteristics may be recorded. This information may be compiled over a period of time so that the microprocessor 14 or other processing means may later read and obtain a performance history of that camera head's use. Such a history may include the total number of uses, total duration of use, and other performance-indicative characteristics such as extreme or average picture levels or white balance levels at which the imager 32 operated.

This history information may help determine when maintenance is necessary based on a certain number of uses, mulative operation time, average picture level approaching tolerance or other maintenance-determining characteristic reflecting component drift. During maintenance, the writing capability of the preferred EEPROM memory device would allow the originally-stored operating parameter information to be erased or altered to reflect how operating parameters may have changed over time. Such alterations ensure that optimum operating conditions are provided to the imager 32 throughout the life of the camera system. This is not possible in camera systems with a "read only" memory device.

In addition to maintenance purposes, tracking imager 32 performance over time may allow manufacturers to understand the working environments in which the camera is used, as well as to understand the camera head itself. For example, if this tracking feature is incorporated into a camera head which undergoes sterilization for medical use such as that described in pending U.S. application Ser. No. 08/018,053 incorporated by reference above, data may be written to the memory device 34 identifying each time the camera head 3 was sterilized. For example, if the camera head 3 is operated for longer than a certain amount of time in one use, e.g., twenty minutes, it may be presumed that the camera head 3 was sterilized for that use. Thus for uses of such duration, information that sterilization occurred may be written to memory device 34 as well as data representing the average picture level at which the imager 32 operated. The sterilization temperature, if known, might also be written to memory device 34. This provides a record of the number of sterilizations experienced by the camera head 3, the temperatures at which the sterilizations occurred, as well as any trends in white balance and picture level data thereby aiding manufacturers to understand effects of temperature on the CCD color filters which may become more transparent over time due to heat. And as discussed above, any performance drift due to heat or other condition may be rectified by writing changed operating parameters to the memory device 34 so that control unit 1 may properly adjust the control circuitry for subsequent camera system operation. The camera head 3 essentially learns from its past experiences and may be adapted.

The writing capability of the preferred memory device 34 also provides flexibility regarding camera system use in the field. For example, maintenance may be effected in the field as changed operating parameters may be written to the memory device to rectify component drift. As another example in the field of endoscopy, despite whatever data might be initially stored in memory device 34 at the factory, or if data is not so initially stored, the user or field representative may assign particular operating parameter or image processing information to the camera head 3 to describe the imager 32, and the endoscope 7 to which the camera head 3 will be attached. This informs the control unit 1 as to the specifics of the imager 32 and endoscope 7 which in turn provides optimum picture processing. Should it be necessary to repeatedly attach different endoscopes having different characteristics to the camera head 3, the information in memory device 34 may be changed repeatedly so that the control unit 1 always knows what signals to send to the camera head 3 for optimum video display. In similar fashion, specific user information such as preferred white balance, picture level, auto exposure performance and doctor name may also be stored.

In summary, the writing capability of memory device 34 allows the camera system to recall details of past experiences to provide a history of use, and also allows alteration by the user to compensate for the effects of age or other changing conditions, or to ensure that the camera system performs to the user's specific needs.

How the invention provides for a camera system of reduced size and using a reduced number of electrical lines is now further described. Preferably, memory device 34 is an EEPROM which provides reading and writing capability, is non-volatile and yet is small enough to fit inside a sufficiently small camera head 3 for use in procedures such as endoscopy (which requires a small, lightweight camera system for easy manipulation by the physician), or industrial applications offering little space for the camera head 3. That memory device 34 is remote from microprocessor 14 or other suitable processing means such as programmable logic, also allows camera head 3 to be sufficiently small because the microprocessor 14 or other processing means which are typically larger than an EEPROM, need not be contained in the camera head 3. Locating a microprocessor or other processing means in the camera head 3 to provide reading and writing capabilities would result in the camera head 3 being too large for endoscopic or other applications operating under tight space constraints.

Besides providing for a smaller-sized camera head 3, the preferred embodiment requires fewer electrical lines to transmit information. As mentioned above, the reading and writing functions via the serial clock and data signals on lines 42 and 52 preferably occur during the turn-on or turn-off phases of the camera head's use and not during the time when imager 32 is actually generating video signals. This permits that the H timing and bias signals transmitted during imager 32 operation, may be transmitted along these same lines 42 and 52 when the CCD 32 generates video signals.

This line-sharing capability reduces the number of lines necessary to transmit electrical information thereby reducing the size of cable 5 and increasing its flexibility which may be advantageous in applications such as endoscopy where the physician must manipulate the camera head 3. This reduction in lines also reduces the cost of the camera system because the cable 5 and associated connectors contain fewer components and are smaller. Furthermore, the risk of malfunction is reduced because there are fewer lines and cable/connector interfaces.

The video camera system described above provides advantages and thereby solves existing problems in the video camera field. The capability to store information representing optimum operating conditions of the imager such as a CCD allows the camera head to be self-describing and interchangeable with control units without sacrificing video display quality and time-consuming adjustments to the control unit. The capability to write information reflecting use of the camera system provides a performance history helpful for use in the field, maintenance purposes and in allowing one to understand the environment in which the camera system is used. Further advantages will be recognized by those skilled in the art.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. An endoscopic video camera system, comprising:
    control circuitry for actuating an imager to produce a video signal and for processing the video signal produced by the imager;

a camera head configured for placement along an optical path extending through an endoscope, and also configured to be detachably and remotely coupled to the control circuitry through at least one signal line, said camera head comprising:
an imager for producing a video signal upon being actuated by control circuitry; and
a readable and writeable non-volatile semiconductor memory device;
said control circuitry further comprising:
a processor which is configured, upon said camera head being operatively engaged to said control circuitry, to read first data representative of at least one characteristic associated with the camera head and stored in said memory device.

2. The endoscopic video camera system of claim 1 wherein the processor is further adapted to configure said control circuitry responsive to the data stored in said memory device, thus adapting said control circuitry to said camera head.

3. The endoscopic video camera system of claim 2 wherein said control circuitry is configured to actuate said imager through at least one signal transmitted over said at least one signal line, and said control circuitry is configured to modify said at least one signal responsive to the first data read from said memory device.

4. The endoscopic video camera system of claim 1 wherein said at least one characteristic includes a characteristic of said imager.

5. The endoscopic video camera system of claim 1 wherein said at least one characteristic includes a characteristic of said endoscope.

6. The endoscopic video camera system of claim 1 wherein said first data is predetermined data stored in said memory device during manufacture of said camera head.

7. The endoscopic video camera system of claim 1 wherein said first data is written into said memory device after manufacture of said camera head.

8. The endoscopic video camera system of claim 1 wherein said processor is configured to update second data stored in said memory device indicative of the number of times the camera head has been used.

9. The endoscopic video camera system of claim 1 wherein said processor is configured to update second data stored in said memory device indicative of the number of times the camera head has been sterilized.

10. The endoscopic video camera system of claim 1 wherein said memory device is an EEPROM.

11. The endoscopic video camera system of claim 1 wherein the camera head is configured for coupling to a proximal end of an endoscope through an optical coupler.

12. An endoscopic video camera system, comprising:
control circuitry for actuating an imager to produce a video signal and for processing the video signal produced by the imager;
a camera head configured for placement along an optical path extending through an endoscope, and also configured to be detachably and remotely coupled to the control circuitry through at least one signal line, said camera head comprising:
an imager for producing a video signal upon being actuated by control circuitry; and
a readable and writeable non-volatile semiconductor memory device; and
said control circuitry further comprising:
a processor which is configured, upon said camera head being operatively engaged to said control circuitry, to access said memory device through said at least one signal line throughout a first time period, and said control circuitry is configured to actuate said imager over said at least one signal line during a second time period which is distinct from and does not overlap the first time period.

13. A method for determining the number of times an endoscopic camera head has been sterilized comprising the steps of:
providing a sterilizable camera head configured for placement along an optical path extending through an endoscope and also including a readable and writeable non-volatile semiconductor memory device for storing data representative of the number of times the camera head has been sterilized;
storing in said memory device first data representative of the number of times the camera head has been sterilized;
predetermining second data representative of the number of sterilization cycles to which said camera head should be limited; and
comparing said first data with said second data and either (1) permitting continued use of said camera head if the number of sterilization cycles to which said camera head should be limited exceeds the number of times the camera head has been sterilized; or (2) providing an end-of-life signal if the number of sterilization cycles to which said camera head should be limited is less than the number of times the camera head has been sterilized.

14. A method for adjusting at least one operating parameter of a semiconductor imager in an endoscopic camera head comprising the steps of:
providing a camera head configured for placement along an optical path extending through an endoscope, and also including:
a semiconductor imager having at least one predetermined operating parameter and configured to produce a video signal upon being actuated by control circuitry; and
a readable and writeable non-volatile semiconductor memory device for storing data representative of said at least one operating parameter;
storing data representative of said at least one operating parameter in said memory device;
providing control circuitry for actuating a semiconductor imager in a camera head and for processing the video signal produced by said imager;
operatively engaging said camera head and said control circuitry, and reading said data representative of said at least one operating parameter from said memory device included in said camera head; and
adjusting said control circuitry responsive to said data to provide said at least one operating parameter to said semiconductor imager.

15. A method for interchanging first and second endoscopic video camera heads comprising the steps of:
providing a first camera head configured for placement along an optical path extending through an endoscope, and also including:
a semiconductor imager configured to produce a video signal upon actuation by control circuitry, said semiconductor imager having a first operating parameter; and
a readable and writeable non-volatile semiconductor memory device for storing data representative of the number of times the camera head has been used;

providing control circuitry for actuating a semiconductor imager in a camera head and for processing the video signal produced by said imager, and also configured to provide said first operating parameter to said semiconductor imager in said first camera head;

storing in said memory device first data representative of the number of times the first camera head has been used;

predetermining second data representative of the number of uses to which said first camera head should be limited;

comparing said first data with said second data and either (1) permitting continued use of said first camera head if the number of uses to which said first camera head should be limited exceeds the number of times the first camera head has been used; or (2) providing an end-of-life signal if the number of uses to which said first camera head should be limited is less than the number of times the camera head has been used;

providing a second camera head configured for placement along an optical path extending through an endoscope, and also including:

a semiconductor imager having a second operating parameter and configured to produce a video signal upon being actuated by control circuitry; and a readable and writeable non-volatile semiconductor memory device for storing data representative of said second operating parameter;

storing data representative of said second operating parameter in said memory device of said second camera head;

performing the following steps if the number of uses to which said first camera head should be limited exceeds the number of uses to which said first camera head should be limited;

operatively engaging said second camera head and said control circuitry, and reading said data representative of said second operating parameter from said memory device included in said second camera head; and adjusting said control circuitry responsive to said data to provide said second operating parameter to said semiconductor imager in said second camera head.

* * * * *

UNITED STATES PATENT AND TRADEMARK OFFICE
CERTIFICATE OF CORRECTION

PATENT NO. : 5,896,166

DATED : April 20, 1999

INVENTOR(S) : D'Alfonso et al.

It is certified that error appears in the above-identified patent and that said Letters Patent is hereby corrected as shown below:

On the cover page, [63] (Continuation information) : insert --which is a Continuation of 08/071,189, June 2, 1993.--

Column 12; Line 12; Claim 15: delete [uses to which] and insert --times--;

Signed and Sealed this

Fourteenth Day of December, 1999

Attest:

Attesting Officer

Q. TODD DICKINSON

Acting Commissioner of Patents and Trademarks